United States Patent [19]
Byrns

[11] 3,932,153
[45] Jan. 13, 1976

[54] NEBULIZER BACTERIA FILTER
[76] Inventor: John Byrns, 7112 Kittyhawk Ave., Los Angeles, Calif. 90045
[22] Filed: May 23, 1974
[21] Appl. No.: 473,141

Related U.S. Application Data
[63] Continuation-in-part of Ser. No. 442,682, Feb. 14, 1974, abandoned.

[52] U.S. Cl. .................. 55/511; 210/445; 210/446
[51] Int. Cl.² ......................................... B01D 27/08
[58] Field of Search ..................... 55/498, 502–510, 55/501, 511; 210/446, 445, 450, 232, 493, 489; 21/94

[56] References Cited
UNITED STATES PATENTS

| | | | |
|---|---|---|---|
| 3,002,870 | 10/1961 | Belgarde et al. | 55/503 |
| 3,341,022 | 9/1967 | Isreeli | 210/232 |
| 3,473,301 | 10/1969 | Buckman | 55/510 |
| 3,574,529 | 4/1971 | Larro | 21/94 |
| 3,651,947 | 3/1972 | Schollhamer | 210/489 |
| 3,782,083 | 1/1974 | Rosenberg | 55/502 |
| 3,785,129 | 1/1974 | Szmutko | 55/505 |

*Primary Examiner*—Bernard Nozick
*Attorney, Agent, or Firm*—Burton, Crandell & Polumbus

[57] ABSTRACT

A bacteria filter includes a pair of generally conical housing sections having confronting marginal flanges adapted to be welded together to seal the sections into an integral filter housing. The flanges have a pair of tongue-in-groove connectors to facilitate alignment of the sections during assembly and to automatically stretch a filter element between the two sections during assembly to optimize the filtering capacity of the filter. Each section of the filter device has a co-axial tubular neck extension defining an inlet and outlet of the filter device.

2 Claims, 7 Drawing Figures

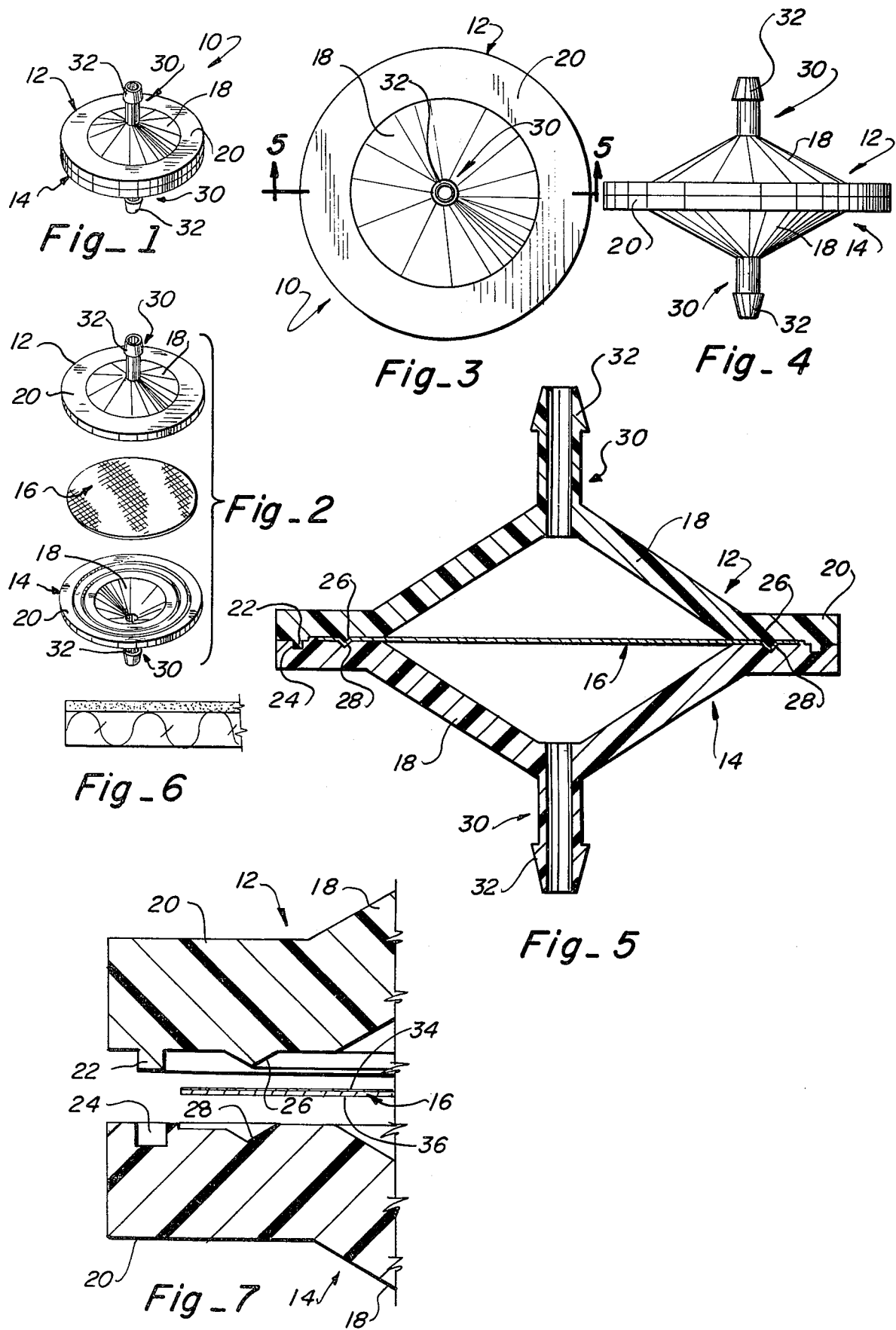

NEBULIZER BACTERIA FILTER

This application is a continuation-in-part of my application Ser. No. 442,682 filed Feb. 14, 1974 now abandoned.

BACKGROUND OF THE INVENTION

1. Field of the Invention

The present invention relates generally to filter devices and more particularly to a new and improved bacteria filter device designed to automatically condition a filter element during assembly for optimum filtering capacity and to the method of assembling the filter device.

2. Description of the Prior Art

In certain artificial respiratory systems, such as intermittent positive pressure breathing apparatus (IPPB) used in assisting asthma patients with breathing, air purifiers or bacteria filters are used to remove undesirable bacteria from the fluid sprayed into the patient's mouth. The IPPB system has a nebulizer nozzle designed to spray the desired fluid into the patient's mouth and the nozzle frequently includes a bacteria filter to purify the air before passage into the patient's mouth. It is important that these filters be simple and compact in construction yet leak-proof so that all air passing through the filter is subjected to the filtering medium and bacteria is reliably removed therefrom. In the past it has been difficult to obtain the desired leak-proof construction without the use of clamping devices to effect the desired seal and the use of such clamping devices renders the filter undesirable for use with nebulizer nozzles because of the bulkiness and complexity of construction.

SUMMARY OF THE INVENTION

It is an object of the present invention to provide a new and improved filter device of simplified construction and a method of assemblying the filter device.

It is another object of the present invention to provide a new and improved compact bacteria filter designed to optimize the removal of bacteria from an air stream.

It is another object of the present invention to provide a filter device which during assembly automatically stretches or tensions a filter element so that the cross-sectional area of the openings in the filter element are decreased from their normal size to optimize the filtering affect upon bacteria being trapped by the filter.

It is another object of the present invention to provide a filter device which is comprised of two sections which have been designed to be integrated by sonic welding or the like and to automatically grip a filter element during assembly to circumferentially stretch the filter element to decrease the cross-sectional area of the openings in the filter element.

These and other objects of the present invention are obtained with a simplified and compact filter device that is easily assembled with three component parts to obtain the desired optimum filtering capacity.

More particularly, the device includes two housing sections having confronting flanges which have been designed to grip and stretch a filter element sandwiched therebetween when the confronting flanges are compressed against each other. The flange of one section has a pair of continuous grooves therein while the confronting flange of the other section has a pair of aligned continuous protrusions or beads adapted to be received in the grooves in the first section. One mating groove and protrusion is adapted to facilitate alignment and positive integral connection of the sections during assembly while the other groove and protrusion serves to grip and apply an outward stretching force to the filter element uniformly in all directions and to establish a positive leak-proof seal between the filter and the opposing or confronting sections.

Each section, of course, has an opening passing therethrough, one of which serves as an inlet to the filter and the other the outlet. In assembly of the filter device, the sections are placed in confronting relationship with the filter element sandwiched therebetween so that the protrusions mate with the associated grooves. The flanges are then sonically welded to be positively bonded together in sealed integral relationship with a peripheral area of the filter element so that the device is leak-proof and will affectively trap bacteria entrained by fluid passed through the device.

Other objects, advantages and capabilities of the present invention will become more apparent as the description proceeds taken in conjunction with the accompanying drawings.

BRIEF DESCRIPTION OF THE DRAWINGS

FIG. 1 is a perspective view of the filter device of the present invention,

FIG. 2 is an exploded perspective view of the filter device of FIG. 1,

FIG. 3 is an enlarged top plan view of the filter device of FIG. 1,

FIG. 4 is an enlarged side elevation of the filter device of FIG. 1,

FIG. 5 is an enlarged section taken along line 5—5 of FIG. 3,

FIG. 6 is an enlarged fragmentary vertical section taken through the filter element of the filter device of FIG. 1, and FIG. 7 is an enlarged fragmentary vertical section taken through the filter device of FIG. 1 with the sections of the filter device spaced from the filter element.

DESCRIPTION OF THE PREFERRED EMBODIMENT

Referring first to FIGS. 1 through 5, the filter device 10 of the present invention is seen to include upper and lower housing sections 12 and 14 respectively, positioned in confronting relationship with a filter element 16 sandwiched therebetween. For purposes of description and not limitation, the upper section 12 may be termed an inlet section and the lower section 14, the outlet section, it being understood that depending upon the type and/or orientation of the filter element 16, that either section could serve as the inlet or outlet section.

Each of the inlet and outlet sections 12 and 14 respectively, can be seen to have a conically shaped body portion 18 with a peripheral or marginal ring-like flange 20 extending radially outwardly from the base of the conical body portion 18.

Referring to FIGS. 5 and 6, the flange 20 of the inlet element 12 has an annular protrusion 22 on its lower face spaced slightly inwardly from the outer periphery of the flange. The protrusion 22 is continuous around the periphery of the flange 20 and in the disclosed form, is of rectangular transverse cross-section. The outlet element 14 has a mating annular groove 24, also of rectangular transverse cross-section in its upper surface adapted to receive the annular protrusion 22 on the inlet element. Therefore, the annular groove 24 and protrusion 22 are equally spaced inwardly from the outer periphery of the respective flanges. Spaced radially inwardly from the annular protrusion 22 on the lower face of the flange of the inlet element 12 is an annular ridge 26 of triangular transverse cross-section which is slightly spaced in a radial direction outwardly from the innermost periphery of the flange 20. The outlet element 14 similarly has an annular groove 28 of triangular transverse cross-section slightly spaced radially outwardly from the innermost periphery of the flange 20 in a position to receive the annular ridge 26 on the inlet element. Accordingly, when the inlet and outlet elements are placed in confronting relationship, as illustrated in FIG. 5, the annular protrusion 22 and the annular ridge 26 project into and mate with the corresponding grooves 24 and 28 respectively, provided in the flange of the outlet element.

At the apex of the conical body portion 18 of each section and extending along the central longitudinal axis of the section is a generally cylindrically shaped rigid tubular neck 30 having a continuous passing therethrough establishing communication between the ambient environment and an enclosed cavity formed by the conical body portions 18 of the sections when they are disposed in confronting engagement as shown in FIG. 5. Each neck 30 has a frusto-conical head 32 on its distal end which serves as a gripping means for a flexible elastic tube (not shown) of a conventional type used to transmit fluids into and out of the filter device 10. Accordingly, as best illustrated in FIG. 5, the elements 12 and 14, when placed in confronting relationship with the filter element 16 sandwiched therebetween establish a confined passage through the filter device which is bisected by the filter element so that fluid flowing through the filter device must pass through the filter element.

Referring to FIG. 6, the filter element 16, which in the preferred form is primarily adapted for filtering bacteria out of dry fluids, is a thin flexible circular disk having a porous, teflon impregnated micro-glass fiber sheet 34 on one face and a laminated sheet 36 of nylon or glass cloth reinforcement on the other face. It is to be noted that the filter element 16 could be any suitable filtering medium having the characteristics desirable for a particular application even though for best results, the filtering element should be virtually inextensible so that it can be stretched tightly between the flanges of the housing sections as described hereinafter. In the disclosed form, the filter element 16 is positioned between the inlet and outlet elements 12 and 14 respectively, so that an outer peripheral area of the filter element lies between the confronting flanges 20 of the elements with the porous, teflon impregnated micorglass fiber face 34 of the filter element facing the inlet element 12.

In assemblying the device, the filter element 16. is placed upon the outlet element 14 so as to overlie the innermost groove 28 in the upper surface of the flange 20. The inlet element 12 is then placed upon the outlet element 14 so that the flanges 20 are in face-to-face relationship with the filter seat 16 disposed therebetween. The inlet and outlet elements are easily aligned with the annular protrusion 22 on the flange of the inlet element 12 which fits into the outermost annular groove 24 in the flange of the outlet element 14. When the elements are appropriately aligned and positioned, as in FIG. 5, the circular ridge 26 on the inlet element overlies the filter sheet 16 so that when the inlet element 12 is moved axially and compressed against the outlet element 14, the filter sheet is depressed along a continuous circular path into the groove 28 which radially stretches and tensions the filter sheet 16 between the housing sections. It should be appreciated that the housing sections are compressed against each other only by axial movement along the central longitudinal axes of the sections so that the filter element 16 is uniformly stretched in a radial direction through 360°. Accordingly, it is not necessary to twist or pivot the sections relative to each other when assembling the device as this could distort or wrinkle the filter element possibly decreasing the efficiency of the device.

With the device assuming the orientation shown in FIG. 5, it is placed in a conventional sonic welding apparatus (not shown) which sonically welds the flanges 20 of the two elements into an integral unified flange thereby sealing the filter sheet 16 between the elements and establishing a circumferential hermetic seal so that fluids passing through the device must pass through the filter sheet. Preferably, the housing sections 12 and 14 are made of a polycarbon plastic material which is well-suited for sonic welding operations. In production, polycarbon housing sections have been suitably welded by applying a force of 40 lbs. to the flanges of the sections for 1.1 seconds during actual welding and leaving the 40 lbs. pressure on the sections for an additional 0.4 seconds while the sections cool.

After the device has been assembled and fully integrated as described, the device may be autoclaved, depending upon its intended use, by passing steam through the device at approximately 300°F for approximately fifteen minutes. The autoclaving treatment not only sterilizes the filter but also shrinks and thereby further tensions the filter element 16 to further reduce the cross-sectional area of the openings in the filter element improving the effectiveness of the filter device 10. After autoclaving, and in actual production, the aforedescribed laminated filter element 16 retained between polycarbon housing sections has been tensioned to approximately 160 PSI and will withstand pressures of 90–135 PSI with a pressure drop of approximately 0.3 to 0.75 PSI at an air flow rate of 10 liters per minute.

It will be appreciated, that the filter device 10 of the present invention is easily assembled through use of an alignment tongue-in-groove system, and the filter sheet 16 is automatically radially tensioned for optimum filtering conditions. When the filter sheet is initially tensioned during assembly of the elements, it will be appreciated that the size of the openings in the filter sheet are reduced and that upon autoclaving, the openings in the filter are further reduced to further increase the filtering capacity.

Through experiments, it has been discovered that the rate at which the housing sections are compressed together has a bearing on the uniformity and degree of tensioning obtained in the filter element. It has been found that by compressing the housing sections together at a rate of 300 inches per second, optimum tension can be placed on the filter element.

Although the present invention has been described with a certain degree of particularity, it is understood that the present disclosure has been made by way of example and that changes in details of structure may be made without departing from the spirit thereof.

What is claimed is:

1. A filter device comprising in combination a pair of housing sections, each section having an opening therethrough and a peripheral flange in confronting relationship with the peripheral flange of the other section to define an enclosed chamber, a continuous ridge on the peripheral flange of one section and a continuous complementary groove on the flange of the other section adapted to receive said ridge, an annular protrusion in the peripheral flange of said one section spaced from and radially outwardly of said ridge, a second groove in said flange of said other section radially spaced outwardly from said complementary groove to receive the protrusion on the flange of said one section and align said sections with respect to each other, a planar filter element disposed between said sections and extending radially outwardly of said flange to an extent sufficient to overlie said radially innermost groove and ridge such that the ridge on the one flange forces a portion of the filter into the groove of the flange of the other section and the protrusion on the one flange and the second groove on the flange of said other section cooperate to align said housing sections while simultaneously tensioning said filter element, and means uniting said housing sections and said filter element along the peripheral surface of said flanges to seal the filter element in said chamber.

2. The filter device of claim 1 wherein said annular protrusion and said second annular groove constituting an aligning means for said housings are disposed radially outwardly from the annular ridge and the first annular groove constituting the tensioning means for said filter, said filter element dimensioned to extend radially beyond said tensioning means and terminating short of said aligning means.

* * * * *